United States Patent [19]

Kageyama et al.

[11] 4,341,659
[45] Jul. 27, 1982

[54] CATALYTIC COMPOSITION

[75] Inventors: Yoichi Kageyama, Isehara; Masakatsu Hatano, Yokohama; Toru Koyama, Machida; Takao Kaneko; Masayosi Murayama, both of Yokohama; Kazunori Oshima, Tokyo, all of Japan

[73] Assignee: Mitsubishi Chemical Industries, Limited, Tokyo, Japan

[21] Appl. No.: 171,242

[22] Filed: Jul. 22, 1980

[51] Int. Cl.³ .................. B01J 27/14; B01J 27/24; B01J 29/16; B01J 29/00
[52] U.S. Cl. .................. 252/435; 252/437; 252/438; 252/456; 252/458; 252/469
[58] Field of Search ............ 252/435, 437, 438, 456, 252/458, 469

[56] References Cited

U.S. PATENT DOCUMENTS 3,773,692 11/1973 Hensel et al. ............... 252/456 X
3,821,324 6/1974 Rentus ........................ 252/469 X Primary Examiner—Delbert E. Gantz
Assistant Examiner—William G. Wright
Attorney, Agent, or Firm—Oblon, Fisher, Spivak, McClelland & Maier

[57] ABSTRACT

There is disclosed a catalytic composition represented by the formula:

$$(Mo)_a(W)_b(Bi)_c(Pb)_d(Sb)_e(K)_f(P)_g(O)_h$$

in which a, b, c, d, e, f, g and h stand for the numbers of atoms for molybdenum, tungsten, bismuth, lead, antimony, potassium, phosphorus and oxygen elements respectively, wherein, given that $a+b=12$,
$0 \leq b \leq 7$
$0.4 \leq c \leq 7$
$2 \leq d \leq 12$
$0.005 \leq e/a \leq 1.14$
$0 \leq f/a \leq 0.136$
$0 \leq g/a \leq 0.54$, and h is one-half the sum of the products of the valences and the numbers of atoms for the individual constituent elements other than oxygen.

3 Claims, No Drawings

CATALYTIC COMPOSITION

BACKGROUND OF THE INVENTION

1. Field of the Invention

This invention relates to catalytic compositions, and more particularly to catalytic compositions which exhibit a marked catalytic effect on the formation of unsaturated nitriles by vapor-phase reaction of an olefin, ammonia and oxygen or an oxygen-containing gas, particularly on the formation of acrylonitrile by vapor-phase reaction of propylene, ammonia and oxygen or an oxygen-containing gas.

2. Description of the Prior Art

Various catalysts have heretofore been proposed for the production of acrylonitrile by vapor-phase catalytic ammoxidation of propylene. It is known in the art that a catalyst comprising molybdenum and bismuth as primary components and further containing such metallic elements as iron, nickel, cobalt and the like can be used to produce acrylonitrile in relatively good yield. However, when such a catalyst is used under the conditions where the gaseous materials are fed into the catalyst bed at a high space velocity and where the conversion of propylene is increased, the selectivity of the catalyst is so decreased that it becomes difficult to achieve a satisfactorily good yield of acrylonitrile. During our study with the intention of developing a catalyst which is capable of producing acrylonitrile with high selectivity even in the case where the gaseous materials are fed at a high space velocity and where the conversion of propylene is increased, we found and disclosed in our co-pending application (Japanese Patent Application Laid-Open (KOKAI) No. 110997/1979) that a catalyst comprising molybdenum, tungsten, bismuth, lead and oxygen within a certain range of composition can be used to produce acrylonitrile in good yield even under the conditions where both the space velocity of the gaseous materials and the conversion of propylene are increased over the prior art molybdenum-bismuth catalysts.

SUMMARY OF THE INVENTION

Upon our further study, we have now found that a further improved yield of acrylonitrile can be attained by use of a catalyst comprising molybdenum, bismuth, lead, antimony, oxygen and optionally tungsten, potassium and/or phosphorus within a certain range of composition, and accomplished this invention.

It is an object of this invention to provide an improved catalytic composition which can be used in commercial production of unsaturated nitriles including acrylonitrile to advantage. In accordance with the present invention, the above-mentioned objective is accomplished by a catalytic composition having the formula:

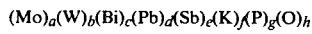

in which a, b, c, d, e, f, g and h stand for the numbers of atoms for molybdenum, tungsten, bismuth, lead, antimony, potassium, phosphorous and oxygen elements, respectively, wherein, given that $a+b=12$, $0 \leq b \leq 7$
$0.4 \leq c \leq 7$
$2 \leq d \leq 12$
$0.005 \leq e/a \leq 1.14$
$0 \leq f/a \leq 0.136$
$0 \leq g/a \leq 0.54$, and h is one-half the sum of the products of the valences and the numbers of atoms for the individual constituent elements other than oxygen.

DETAILED DESCRIPTION OF THE INVENTION

As mentioned above, the catalytic compositions of this invention are represented by the formula:

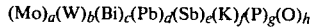

in which a, b, c, d, e, f, g and h stand for the numbers of atoms for molybdenum, tungsten, bismuth, lead, antimony, potassium, phosphorus and oxygen elements, respectively, wherein, given that $a+b=12$, $0 \leq b \leq 7$
$0.65 \leq c \leq 7$
$2 \leq d \leq 12$
$0.005 \leq e/a \leq 1.14$
$0 \leq f/a \leq 0.136$
$0 \leq g/a \leq 0.54$, and h is one-half the sum of the products of the valences and the numbers of atoms for the individual constituent elements other than oxygen.

More specifically, the catalytic compositions of this invention include those represented by any of the formulae:

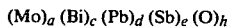

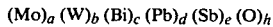

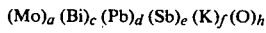

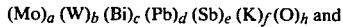

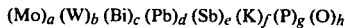

wherein a, b, c, d, e, f, g and h are as defined above. In these formulae, it is preferred in order to improve the selectivity of the catalyst toward the desired unsaturated nitriles that the numbers of atoms for the individual constituent elements (i.e., values, a to g) satisfy the following equations: given that $a+b=12$, $0.08 \leq b \leq 5.5$
$0.67 \leq c \leq 6.3$
$2.6 \leq d \leq 11$
$0.045 \leq e/a \leq 0.68$
$0.004 \leq f/a \leq 0.11$
$0.016 \leq g/a \leq 0.54$ The catalytic composition of this invention may be shaped with or without a carrier material such as silica, titania, alumina, silicon carbide or the like. The size and geometry of the shaped catalyst are not critical and the catalytic composition may be shaped into catalyst particles of any size and geometry (e.g., pellets, tablets, granules, etc.) depending on the conditions under which it is used.

Molybdenum compounds useful for the preparation of the catalytic composition of this invention include molybdenum oxides such as molybdenum trioxide, molybdic acid and its salts, and phosphomolybdic acid and its salts. Preferably molybdates such as ammonium paramolybdate are used. Useful tungsten compounds include tungsten oxides such as tungsten trioxide, tungstic acid and its salts such as ammonium paratungstate, and phosphotungstic acid and its salts. Bismuth compounds that can be used include bismuth salts such as bismuth nitrate and bismuth sulfate and various oxides and hydroxides of bismuth. Useful lead compounds include lead salts such as lead nitrate and lead sulfate and various oxides and hydroxides of lead. Useful antimony compounds include oxides such as antimony trioxide, chlorides such as antimony trichloride and metallic antimony. Useful potassium compounds include potassium salts such as potassium nitrate, potassium carbonate, potassium molybdate, potassium tungstate, potassium phosphomolybdate, potassium phosphtungstate and potassium phosphates, and potassium hydroxide. Useful phosphorus compounds include phosphoric acids such as orthophosphoric acid, heteropolyphosphoric acids such as phosphomolybdic acid and phosphotungstic acid, salts of these acids, and organophosphorus compounds.

The catalytic composition can be prepared from the appropriate combination of these raw materials by dissolving or suspending the compounds of the constituent elements in water to form a uniform aqueous slurry or solution. In some cases, a sol of a carrier material such as silica sol or alumina sol or carrier particles such as titania powder may be suspended in the slurry or solution. The resulting uniform slurry or solution is then evaporated to dryness and shaped in separate steps or in a single step by spray drying and finally calcined in a stream of air to prepare a catalyst. In preparation of the catalyst, when ammonium paramolybdate and/or ammonium paratungstate is used as the molybdenum and/or tungsten source, respectively, a dissolution accelerator such as ammonia is preferably added to the aqueous medium in order to increase the solubility of these compounds. In the case where bismuth nitrate or bismuth sulfate is employed as the bismuth source, it is preferably dissolved in a water acidified with nitric acid or sulfuric acid correspondingly. When antimony trioxide is used as the antimony source, it may be added after it has been dissolved in an aqueous solution of an organic acid such as tartaric acid, or otherwise it may be added directly in the form of powdered antimony trioxode. In the latter case, the resulting final slurry containing all the catalytic components including the antimony trioxide powder can be uniformly stirred, adjusted to pH 7 or less and heated at 40° C. or higher, preferably 80° to 130° C. for at least 30 minutes, preferably 1 to 8 hours to further improve the selectivity of the finally obtained catalytic composition toward unsaturated nitriles. Following the shaping step, the shaped particles are usually calcined for 1 to 4 hours at a temperature in the range of 400° to 800° C., preferably in the range of 500° to 750° C., although the temperature and duration of the calcination step are not critical. The catalytic compositions of this invention can be used in the following way. The following description is limited to the production of acrylonitrile, it is to be understood that the catalytic compositions can be used for the production of other unsaturated nitriles as well. In order to produce acrylonitrile, propylene, ammonia and oxygen or an oxygen-containing gas are contacted in the vapor phase in the presence of a catalyst according to this invention (e.g., one prepared in any of the following Examples). It is not always necessary that the starting propylene gas is of high purity, and the propylene gas may contain a substantial amount of other gas which is substantially inert to the reaction, for example, a saturated hydrocarbon such as propane. The oxygen used may be either pure oxygen gas or diluted with other gas or gases inert to the reaction. In a commercial operation air is usually employed as the oxygen-containing gas. The molar ratio of oxygen to propylene fed to the reaction zone are usually in the range of 1:1 to 4:1, preferably from 1.5:1 to 2.5:1. Ammonia is fed in an amount of 0.8 to 2.5 moles, preferably 0.9 to 1.5 moles per mole of propylene. The vapor-phase reaction is usually conducted at atmospheric pressure, but it may be carried out at a subatmospheric or superatmospheric pressure as required. The reaction temperature is usually from 360° to 540° C., preferably from 400° to 500° C. The space velocity at which the gaseous reactants are fed may suitably be selected from the range of 100 to 3,000 hr$^{-1}$, preferably 200 to 2,000 hr$^{-1}$.

The catalytic compositions of this invention may be used either in the fixed or fluidized bed system.

As previously mentioned, the catalytic compositions of this invention are capable of formation of acrylonitrile with high selectivity even at an increased conversion of the starting gaseous material and hence they can be employed in the commercial production of acrylonitrile to advantage.

Having generally described the invention, a more complete understanding can be obtained by reference to certain examples which are provided herein for purposes of illustration only and are not intended to be limiting in any manner.

The terms "conversion", "selectivity" and "yield of acrylonitrile" used herein, particularly in the examples are defined by the following equations:

$$\% \text{ Conversion} = \frac{\text{Moles of propylene consumed}}{\text{Moles of propylene fed}} \times 100$$

$$\% \text{ Selectivity} = \frac{\text{Moles of acrylonitrile formed}}{\text{Moles of propylene consumed}} \times 100$$

Yield of acrylonitrile = [% Conversion] × [% selectivity]/100

EXAMPLE 1

In 31.9 ml of water was suspended 1.275 g of commercially available antimony trioxide (Sb$_2$O$_3$) powder and to the resulting suspension were added successively 2.955 g of anatase titanium dioxide (TiO$_2$) powder and a solution of 3.263 g of ammonium paratungstate [(NH$_4$)$_{10}$W$_{12}$O$_{41}$.5H$_2$O] in 100 ml of aqueous 1 wt. % ammonia.

To the slurry, the following sol and solutions were added in that order with stirring: 59 g of 20 wt. % silica sol; a solution of 8.280 g of lead nitrate in 22.5 ml of water; a solution of 4.855 g of ammonium paramolybdate [(NH$_4$)$_6$Mo$_7$O$_{24}$.4H$_2$O] in 25 ml of aqueous 5 wt. % ammonia; and a solution of 4.851 g of bismuth nitrate [Bi(NO$_3$)$_3$.5H$_2$O] in 7.5 ml of aqueous 10 wt. % nitric acid. Thereafter the pH of the slurry was adjusted to 4.0 by addition of an aqueous 10 wt. % nitric acid solution and the slurry was then heated with stirring on a hot plate until the evolution of NO$_2$ ceased and the heating was continued until the slurry was evaporated to dryness. The solid residue was compressed into tablets of 6 mm in diameter and 3 mm in thickness, which were then calcined at 550° C. for 2 hours in a stream of air. The tablets were finally crushed to give a catalyst in the form of granules of 16 to 24 mesh (Tyler) in size. The catalyst thus obtained had the composition: Mo$_{8.25}$ W$_{3.75}$ Bi$_{3.00}$ Pb$_{7.50}$ Sb$_{2.62}$ O$_{51.93}$ which was supported on a carrier comprising silica and titania. The weight ratio of silica to titania to total catalytic components was 40:10:50.

A Pyrex reactor of 4 mm inner diameter was packed with 1 ml of the supported catalyst as prepared above. A mixed gas of propylene, ammonia and air having a molar ratio of propylene to ammonia to air of 1:1.2:10 was passed at a space velocity of 500 hr$^{-1}$ through the catalyst bed in tubular reactor held at 470° C. to produce acrylonitrile. The results were 97.4% conversion of propylene and 85.2% selectivity toward acrylonitrile (with 83.0% yield of acrylonitrile).

EXAMPLES 2-22

Following the procedure described in Example 1, various catalysts of composition indicated in the following table were prepared and used in the ammoxidation of propylene at temperatures indicated in Table 1. The results are also reported in Table 1.

resulting slurry was adjusted to 4.0 with an aqueous 10 wt. % nitric acid solution.

The slurry was then heated with stirring on a hot plate until the evolution of $NO_2$ gas ceased and it was further heated to dryness. The solid residue was shaped into tablets of 6 mm in diameter and 3 mm in thickness, which were then calcined at 550° C. for 2 hours in a stream of air and crushed to give a catalyst in the form of granules of 16 to 24 mesh (Tyler) in size. The catalyst thus obtained had the composition: $Mo_{11.28}\ W_{0.72}\ Bi_{2.82}\ Pb_{7.74}\ Sb_{3.33}\ K_{0.51}\ O_{53.22}$ and the carrier components, i.e., silica and titania, and the catalytic components were present at the weight ratio of silica to titania to total catalytic components of 40:10:50.

One (1) ml of the supported catalyst as prepared above was placed in the same reactor as used in Exam-

TABLE 1

| Ex. No. | Composition of Catalyst | | | | | | Reaction Temp. (°C.) | % Conversion of Propylene | % Selectivity toward AN* | % Yield of AN* |
| --- | --- | --- | --- | --- | --- | --- | --- | --- | --- | --- |
| | Mo | W | Bi | Pb | Sb | O | | | | |
| 2 | 10.5 | 1.5 | 6.0 | 3.0 | 0.48 | 48.72 | 465 | 99.2 | 80.3 | 79.7 |
| 3 | 8.12 | 3.88 | 4.65 | 5.02 | 2.21 | 53.26 | 486 | 98.3 | 83.7 | 82.3 |
| 4 | 6.42 | 5.58 | 3.36 | 6.97 | 2.68 | 52.03 | 480 | 96.0 | 80.9 | 77.7 |
| 5 | 7.00 | 5.00 | 2.99 | 7.51 | 2.39 | 51.58 | 470 | 97.4 | 82.6 | 80.5 |
| 6 | 12 | 0 | 5.67 | 3.55 | 1.09 | 49.69 | 453 | 98.6 | 82.9 | 81.7 |
| 7 | 6.29 | 5.71 | 2.29 | 8.58 | 2.00 | 51.02 | 485 | 98.9 | 82.3 | 81.4 |
| 8 | 5.33 | 6.67 | 1.33 | 9.98 | 1.99 | 50.96 | 500 | 98.7 | 78.2 | 77.2 |
| 9 | 10.11 | 1.89 | 2.99 | 7.49 | 2.99 | 52.46 | 470 | 97.6 | 85.7 | 83.6 |
| 10 | 11.79 | 0.21 | 3.48 | 6.75 | 2.63 | 51.92 | 450 | 98.5 | 85.9 | 84.6 |
| 11 | 12 | 0 | 3.0 | 7.53 | 3.0 | 52.53 | 462 | 99.5 | 85.0 | 84.6 |
| 12 | 11.28 | 0.72 | 2.82 | 7.74 | 3.85 | 53.75 | 471 | 98.5 | 87.0 | 85.7 |
| 13 | 9.13 | 2.87 | 2.28 | 8.55 | 4.27 | 54.38 | 473 | 98.9 | 85.8 | 84.9 |
| 14 | 11.84 | 0.16 | 2.26 | 8.61 | 4.52 | 54.78 | 472 | 97.0 | 87.4 | 84.8 |
| 15 | 9.71 | 2.29 | 1.85 | 9.27 | 3.71 | 53.61 | 490 | 98.4 | 84.3 | 83.0 |
| 16 | 12.0 | 0 | 1.69 | 2.45 | 0.65 | 41.96 | 463 | 99.0 | 84.9 | 84.1 |
| 17 | 11.48 | 0.52 | 1.62 | 9.55 | 2.40 | 51.58 | 472 | 98.7 | 86.6 | 85.5 |
| 18 | 7.06 | 4.94 | 0.99 | 10.53 | 1.48 | 50.24 | 480 | 98.7 | 78.2 | 77.2 |
| 19 | 11.43 | 0.57 | 0.88 | 10.65 | 1.35 | 50.00 | 473 | 98.3 | 82.8 | 81.4 |
| 20 | 10.03 | 1.97 | 0.78 | 14.95 | 2.10 | 55.27 | 490 | 98.5 | 78.9 | 77.7 |
| 21 | 9.92 | 2.08 | 2.48 | 8.25 | 3.16 | 52.71 | 463 | 96.7 | 86.7 | 83.8 |
| 22 | 11.28 | 0.72 | 2.82 | 7.74 | 3.33 | 52.97 | 470 | 98.8 | 85.5 | 84.5 |

*An = Acrylonitrile

EXAMPLE 23

To a suspension of 1.895 g of antimony trioxide ($Sb_2O_3$) powder in 47.4 ml of water were added successively 3.654 g of anatase titanium dioxide ($TiO_2$) powder and a solution of 0.731 g of ammonium paratungstate [$(NH_4)_{10}W_{12}O_{41}.5H_2O$] in 22.5 ml of aqueous 1 wt. % ammonia.

To the resulting slurry, the following sol and solutions were added in that order with stirring: 73.1 g of 20 wt. % silica sol; a solution of 10.0 g of lead nitrate [$Pb(NO_3)_2$] in 27.2 ml of water; a solution of 7.768 g of ammonium paramolybdate [$(NH_4)_6Mo_7O_{24}.4H_2O$] in 40 ml of aqueous 5 wt. % ammonia; a solution of 5.336 g of bismuth nitrate [$Bi(NO_3)_3.5H_2O$] in 8.3 ml of aqueous 10 wt. % nitric acid; and a solution of 0.138 g of potassium carbonate ($K_2CO_3$) in 5 ml of water. The pH of the ple 1 and the reaction was carried out in the same manner as described in Example 1. At a reaction temperature of 475° C., 97.3% conversion of propylene and 88% selectivity toward acrylonitrile (with 85.6% yield of acrylonitrile) were obtained. It is apparent from the comparison between the results of Examples 22 and 23 that the presence of potassium as a catalytic constituent brings about improved results.

EXAMPLES 24-26

Various potassium-containing catalysts of the composition indicated in Table 2 below were prepared in the same manner as in Example 23 and used in the production of acrylonitrile as in Example 1. The results are also shown in Table 2.

TABLE 2

| Ex. No. | Composition of Catalyst | | | | | | | Reaction Temp. (°C.) | % Conversion of Propylene | % Selectivity toward AN* | % Yield of AN* |
| --- | --- | --- | --- | --- | --- | --- | --- | --- | --- | --- | --- |
| | Mo | W | Bi | Pb | Sb | K | O | | | | |
| 24 | 12 | 0 | 3.55 | 6.65 | 2.67 | 0.22 | 52.09 | 460 | 97.5 | 87.7 | 85.5 |
| 25 | 11.79 | 0.21 | 3.48 | 6.75 | 2.63 | 0.21 | 52.02 | 460 | 98.2 | 86.9 | 85.3 |
| 26 | 9.20 | 2.8 | 3.35 | 7.11 | 2.22 | 0.21 | 51.57 | 480 | 98.4 | 85.9 | 84.5 |

*AN = Acrylonitrile

EXAMPLE 27

To a solution of 1.305 g of ammonium paratungstate [(NH$_4$)$_{10}$W$_{12}$O$_{41}$.5H$_2$O] in 40 ml of aqueous 1 wt. % ammonia was added with stirring 246.2 g of 20 wt. % silica sol, and the following solutions were added with stirring in that order: a solution of 31.464 g of lead nitrate in 61.1 ml of water; a solution of 22.245 g of ammonium paramolybdate [(NH$_4$)$_6$Mo$_7$O$_{24}$.4H$_2$O] in 114.5 ml of aqueous 5 wt. % ammonia; a solution of 11.642 g of bismuth nitrate in 18 ml of aqueous 10 wt. % nitric acid; and a solution of 2.1 g of commercially available antimony trioxide powder dissolved under heating in a mixture of 8.6 ml of water, 1.7 ml of aqueous 25 wt. % ammonia and 3.2 g of tartaric acid. An aqueous 10 wt. % nitric acid solution was then added to the resulting slurry to adjust the pH of the slurry to 4.2. Separately a solution of 69.11 mg of potassium carbonate (K$_2$CO$_3$) in 2.5 ml of water was added to a solution of 1.077 g of phosphotungstic acid (P$_2$O$_5$.24WO$_3$.41.85-H$_2$O) in 5 ml of water to form potassium phosphotungstate as a precipitate. The precipitate-containing reaction mixture was added to the above slurry and the resulting slurry was heated with stirring on a hot plate until the evolution of NO$_2$ ceased, and the heating was continued until the slurry was evaporated to dryness. The solid residue was compressed into tablets of 6 mm in diameter and 3 mm in thickness, which were calcined at 650° C. for 2 hours in a stream of air and then crushed to give a catalyst in the form of granules of 16 to 24 mesh (Tyler).

Using 1 ml of the catalyst thus obtained, the ammoxidation of propylene was carried out under the same conditions as in Example 1. The composition of the catalyst and the results of the ammoxidation reaction including the temperature at which a maximum yield of acrylonitrile was obtained are reported in Table 3.

EXAMPLE 28

The procedure of Example 27 was repeated except that the catalyst was prepared from a slurry which further contained 0.15 g of aqueous 85 wt. % orthophosphoric acid. The composition of the catalyst and the results of the reaction are shown in Table 3.

EXAMPLE 29

To a suspension of 1.75 g of commercially available antimony trioxide powder in 43.8 ml of water was added a solution of 1.305 g of ammonium paratungstate [(NH$_4$)$_{10}$W$_{12}$O$_{41}$.5H$_2$O] in 40 ml of aqueous 1 wt. % ammonia, followed by 163 g of 20 wt. % silica sol with stirring. Thereafter the following solutions were added successively with stirring: a solution of 31.464 g of lead nitrate in 61.1 ml of water; a solution of 22.245 g of ammonium paramolybdate [(NH$_4$)$_6$Mo$_7$O$_{24}$.4H$_2$O] in 114.5 ml of aqueous 5 wt. % ammonia; and a solution of 11.642 g of bismuth nitrate in 18 ml of aqueous 10 wt. % nitric acid. The resulting slurry was adjusted to pH 4.2 with an aqueous 10 wt. % nitric acid solution. Separately a solution of 69.11 mg of potassium carbonate (K$_2$CO$_3$) in 2.5 ml of water was added to a solution of 1.077 g of phosphotungstic acid (P$_2$O$_5$24WO$_3$.41.85-H$_2$O) in 5 ml of water to form potassium phosphotungstate as a precipitate. The precipitate-containing reaction mixture was then added to the above slurry and the resulting slurry was placed in a three-necked flask and heated under reflux for 3 hours at 100° C. During this heating, the pH of the slurry rose from 4.2 to 5.0 and it was readjusted to 4.2. The slurry was then heated with stirring on a hot plate until the evolution of NO$_2$ ceased, whereupon it was evaporated to dryness. The solid residue was compressed into tablets of 6 mm of diameter and 3 mm in thickness, which were calcined at 650° C. for 2 hours in a stream of air and then crushed to give a catalyst in the form of granules of 16 to 24 mesh (Tyler).

Using 1 ml of the catalyst, the ammoxidation of propylene was carried out under the same conditions as in Example 1. The composition of the catalyst and the results of the ammoxidation reaction are shown in Table 3.

EXAMPLE 30

The procedure of Example 29 was repeated except that the heating of the slurry under reflux at 100° C. was omitted. The composition of the catalyst and the results of the ammoxidation reaction are shown in Table 3.

EXAMPLES 31-32

Following the procedure of Example 29, various catalyst of the composition indicated in Table 3 were prepared and used in the ammoxidation of propylene at temperatures indicated in Table 3. The results are also shown in Table 3.

TABLE 3

| Ex. No. | Composition of Catalyst | | | | | | | | Cat./SiO$_2$ Weight Ratio | Reaction Temp. (°C.) | % Conversion of Propylene | % Selectivity toward AN* | % Yield of AN* |
|---|---|---|---|---|---|---|---|---|---|---|---|---|---|
| | Mo | W | Bi | Pb | Sb | K | P | O | | | | | |
| 27 | 11.2 | 0.8 | 2.1 | 8.4 | 1.27 | 0.09 | 0.03 | 49.58 | 50/50 | 470 | 99.3 | 85.9 | 85.3 |
| 28 | 11.2 | 0.8 | 2.1 | 8.4 | 1.27 | 0.09 | 0.14 | 49.85 | 50/50 | 470 | 98.8 | 87.4 | 86.4 |
| 29 | 11.2 | 0.8 | 2.1 | 8.4 | 1.07 | 0.09 | 0.03 | 49.28 | 60/40 | 460 | 99.1 | 87.5 | 86.7 |
| 30 | 11.2 | 0.8 | 2.1 | 8.4 | 1.07 | 0.09 | 0.03 | 49.28 | 60/40 | 460 | 99.6 | 85.5 | 85.2 |
| 31 | 11.2 | 0.8 | 2.1 | 8.4 | 2.1 | 0.09 | 0.03 | 50.82 | 50/50 | 470 | 98.2 | 87.5 | 85.9 |
| 32 | 11.3 | 0.7 | 2.2 | 8.2 | 1.08 | 0.13 | 0.04 | 49.29 | 60/40 | 460 | 98.2 | 88.8 | 87.2 |

*AN = Acrylonitrile

COMPARATIVE EXAMPLE 1

A catalyst having the composition: Mo$_{8.25}$ W$_{3.75}$ Bi$_{3.00}$ Pb$_{7.50}$ O$_{48}$ (supported on a carrier comprising silica and titania at the weight ratio of catalyst to carrier of 50:50) was prepared in the same way as described in Example 1 except that the addition of antimony trioxide (Sb$_2$O$_3$) was omitted, and it was used in the ammoxidation of propylene as in Example 1 at a reaction temperature of 460° C. The results were 98.7% conversion of propylene and 77% selectivity toward acrylonitrile (with 76% yield of acrylonitrile).

COMPARATIVE EXAMPLES 2-4

Various catalysts of the composition indicated in Table 4 were prepared in the same way as in Comparative Example 1 and used in the ammoxidation of propylene as in Example 1 at reaction temperatures indicated in Table 4. The results are also reported in Table 4.

TABLE 4

| Comp. Ex. No. | Composition of Catalyst | | | | | Reaction Temp. (°C.) | % Conversion of Propylene | % Selectivity toward AN* | % Yield of AN* |
| --- | --- | --- | --- | --- | --- | --- | --- | --- | --- |
| | Mo | W | Bi | Pb | O | | | | |
| 2 | 10.5 | 1.5 | 6.0 | 3.0 | 48 | 455 | 99.6 | 74.5 | 74.2 |
| 3 | 12 | 0 | 5.67 | 3.55 | 48 | 455 | 100 | 73.8 | 73.8 |
| 4 | 9.92 | 2.08 | 2.48 | 8.25 | 48 | 464 | 100 | 75.1 | 75.1 |

*AN = Acrylonitrile

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A catalytic composition represented by the formula:

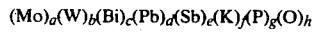

$$(Mo)_a(W)_b(Bi)_c(Pb)_d(Sb)_e(K)_f(P)_g(O)_h$$

in which a, b, c, d, e, f, g and h stand for the numbers of atoms for molybdenum, tungsten, bismuth, lead, antimony, potassium, phosphorus and oxygen elements, respectively, wherein, given that $a+b=12$, $0 \leq b \leq 7$
$0.4 \leq c \leq 7$
$2 \leq d \leq 12$
$0.005 \leq e/a \leq 1.14$
$0 \leq f/a \leq 0.136$
$0 \leq g/a \leq 0.54$, and h is one-half the sum of the products of the valences and the numbers of atoms for the individual constituent elements other than oxygen.

2. The composition of claim 1, wherein said catalyst is supported on a carrier material selected from the group consisting of silica, titania, alumina and silicon carbide.

3. The composition of claim 1, wherein, given that $a+b=12$, the number of atoms are as follows:

$0.08 \leq b \leq 5.5$
$0.67 \leq c \leq 6.3$
$2.6 \leq d \leq 11$
$0.045 \leq e/a \leq 0.68$
$0.004 \leq f/a \leq 0.11$
$0.016 \leq g/a \leq 0.54$.

* * * * *